United States Patent [19]

Nakao et al.

[11] Patent Number: 5,217,001
[45] Date of Patent: Jun. 8, 1993

[54] ENDOSCOPE SHEATH AND RELATED METHOD

[76] Inventors: Naomi L. Nakao, 303 E. 57th St., New York, N.Y. 10022; Peter J. Wilk, 185 W. End Ave., New York, N.Y. 10023

[21] Appl. No.: 803,569

[22] Filed: Dec. 9, 1991

[51] Int. Cl.$^5$ ............................................. A61B 1/00
[52] U.S. Cl. ...................................... 128/4; 24/587
[58] Field of Search ............... 128/4, 11, 16, 6, 917, 128/918, 919, 844; 220/DIG. 7; 383/63; 24/587, 576

[56] References Cited

U.S. PATENT DOCUMENTS

| | | |
|---|---|---|
| 2,548,602 | 4/1951 | Greenburg . |
| 3,495,306 | 2/1970 | Eichberg ............................... 24/576 |
| 3,517,702 | 6/1970 | Mueller et al. ...................... 24/587 X |
| 3,654,049 | 4/1972 | Ausnit ................................. 383/63 X |
| 4,646,722 | 3/1987 | Silverstein et al. . |
| 4,815,470 | 3/1989 | Curtis et al. . |
| 4,858,286 | 8/1989 | Siegel ................................. 383/63 X |
| 4,886,049 | 12/1989 | Darras ....................................... 128/4 |
| 4,898,492 | 2/1990 | Janowski ........................... 24/587 X |
| 5,025,778 | 6/1991 | Silverstein et al. . |

Primary Examiner—Richard J. Apley
Assistant Examiner—Karen A. Jalbert
Attorney, Agent, or Firm—R. Neil Sudol; Henry D. Coleman

[57] ABSTRACT

A device utilizable with an endoscope to promote sterility comprises a substantially thin-walled elongate tubular sheath made of a flexible material such as rubber, the sheath having a use configuration with an inner diameter larger than an outer diameter of an insertion member of the endoscope, whereby the sheath may be removably disposed about such insertion member to substantially surround same prior to insertion of the insertion member into a patient. The device further comprises a transparent cap member and an element or elements for attaching the cap member in a fluid tight seal to a distal end of the sheath so that the cap member covers a distal end of the insertion member of the endoscope. Biopsy channels, some of which are expandable from collapsed configurations to receive endoscopic surgical instruments during an operation, are provided on or in the sheath.

24 Claims, 3 Drawing Sheets

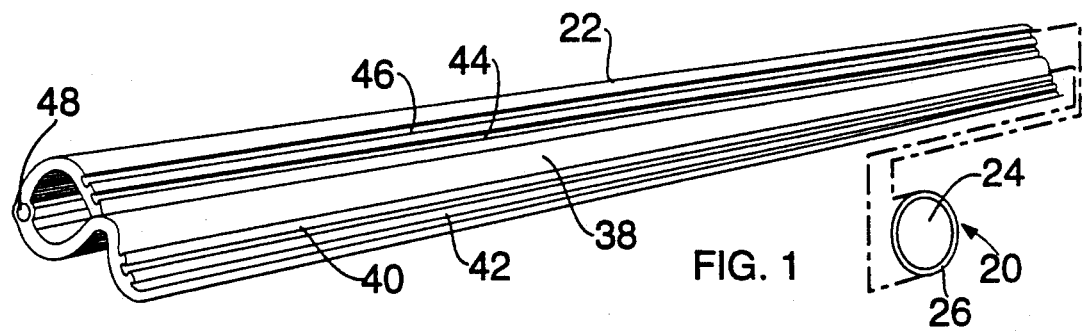
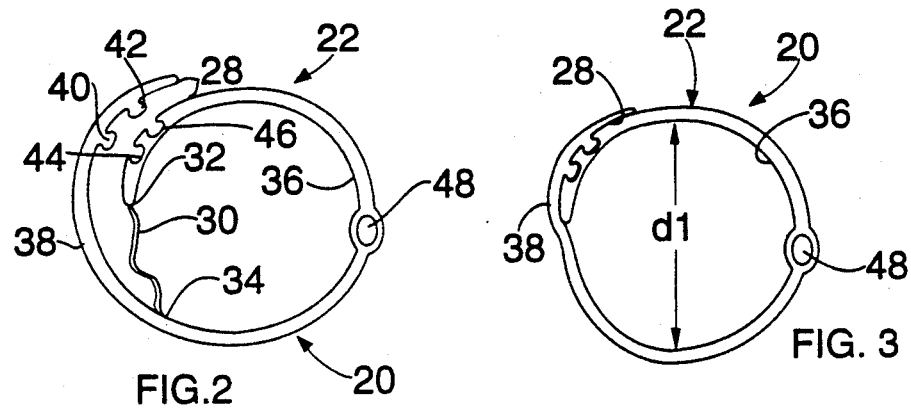
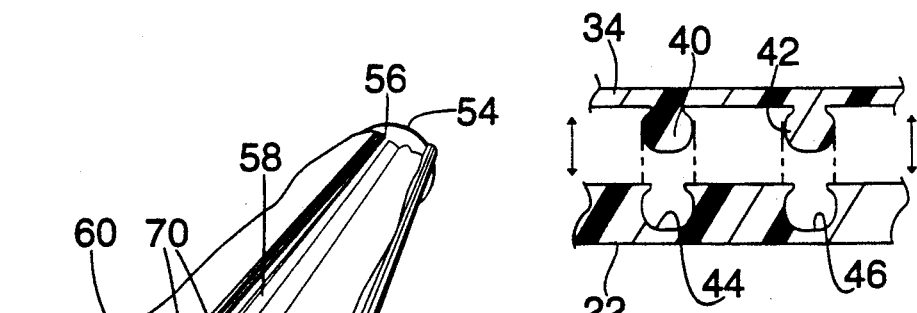
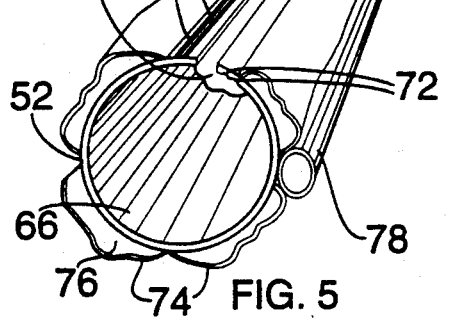
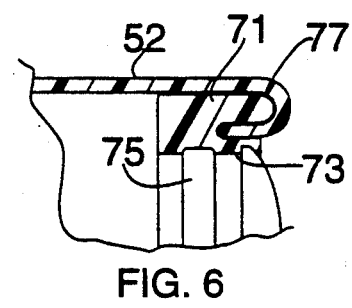

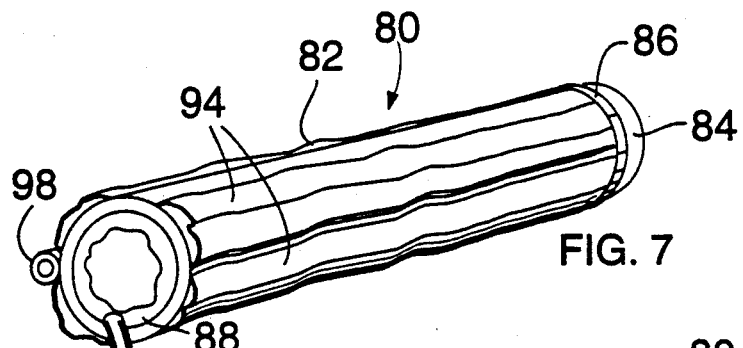
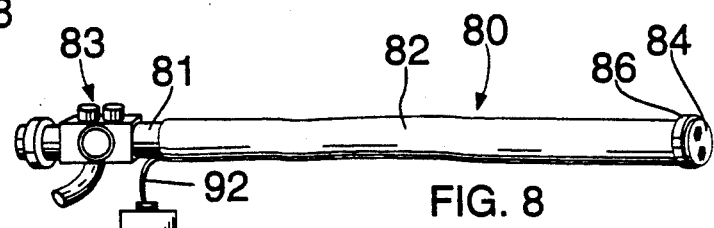
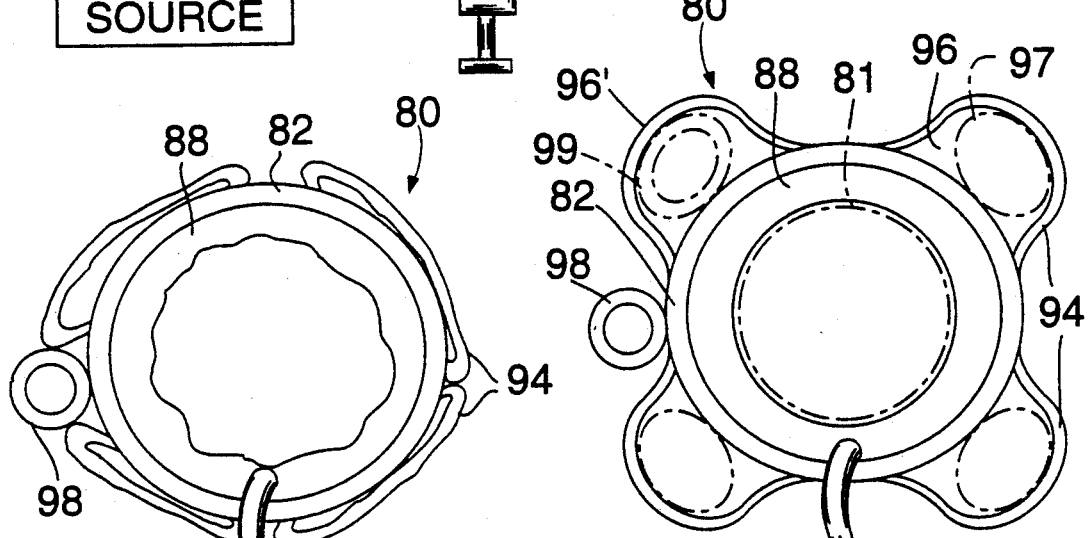
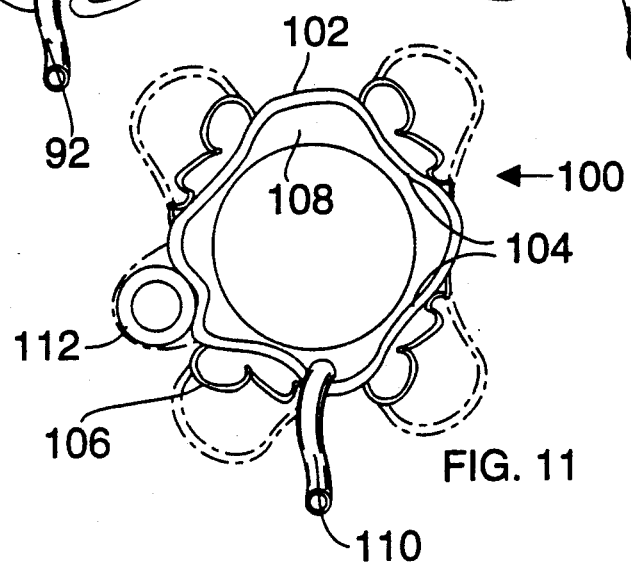

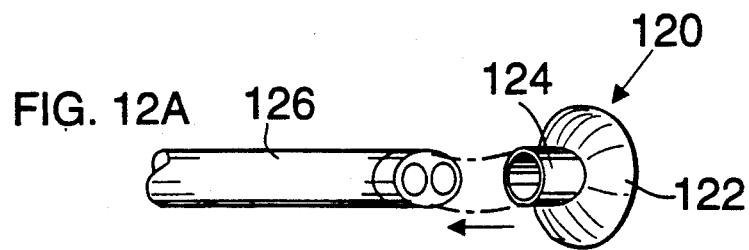
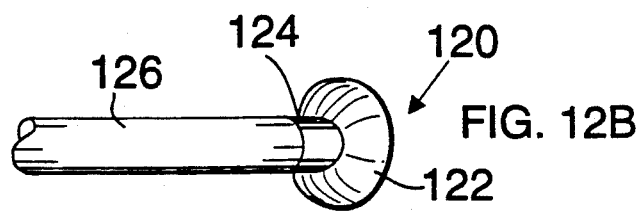
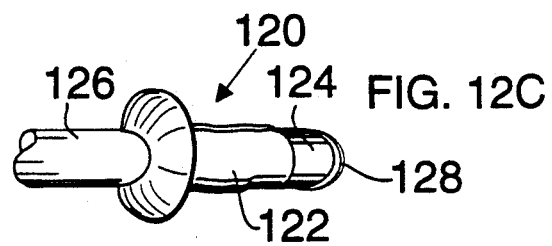
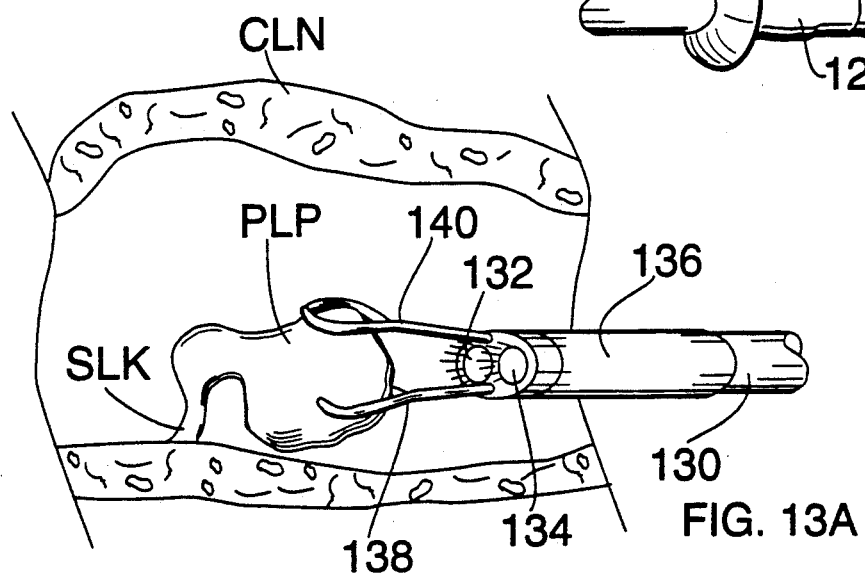
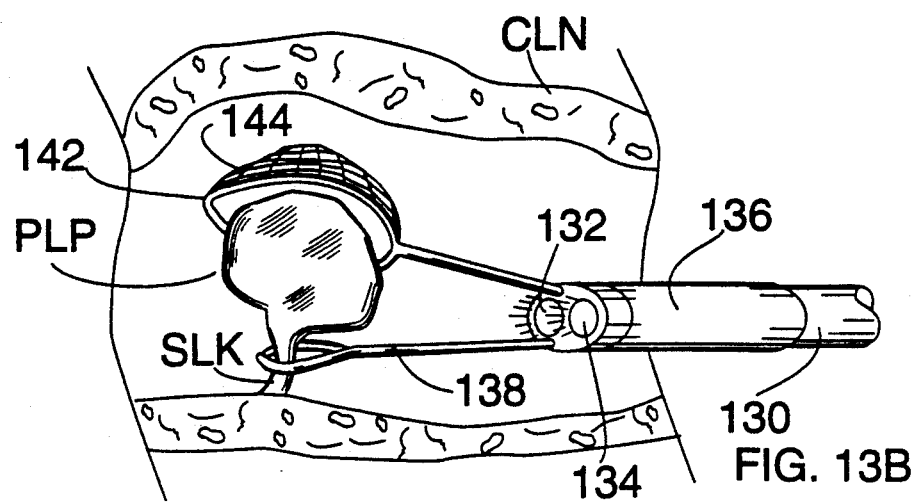

ENDOSCOPE SHEATH AND RELATED METHOD

BACKGROUND OF THE INVENTION

This invention relates to endoscopes and endoscopic surgical procedures. More particularly, this invention relates to a device and an associated method for enhancing sterility in endoscopic surgery. Even more particularly, this invention relates to a sheath member for an endoscope and an associated surgical technique.

Endoscopes are surgical instruments which enable a relatively non-intrusive visual inspection of and surgery on internal body tissues, particularly body tissues located within the digestive tract. An endoscope includes a long flexible tubular member which is inserted into the colon through the anus or into the esophagus through the mouth or the nose.

The tubular insertion member of an endoscope generally includes optical fibers for carrying light energy into the patient and for carrying organized visual information out of the patient. The insertion member also includes an elongate cylindrical channel for inserting a surgical instrument into the patient.

The operating tip of a surgical instrument which is inserted through the ancillary, biopsy, channel of an endoscope is controlled by a surgeon who manipulates an actuator at the proximal end of the endoscope. The operation is visually monitored via the visual feedback information provided by the endoscope. Larger endoscopes, particularly for use in the colon, may contain several ancillary channels, e.g., for applying suction and for feeding water and/or air to the distal end of the endoscope's insertion member.

Because endoscopes are expensive instruments, they are used on multiple patients and must accordingly be sterilized after each procedure. Sterilization generally entails soaking at least the distal end of the endoscope's insertion member in a antibacterial and antiviral solution. In addition, the operating channels of the insertion member must be flushed, preferably with a sterilizing solution.

Such sterilization procedures require substantial amounts of time. Costs are increased, not only because of the hospital personnel time involved, but also because the endoscopes are out of use for that additional time.

Moreover, there is always the risk that sterilization is inadequate and that renegade bacteria or viruses remain in the endoscope and may be subsequently transferred to a patient. This risk cannot be ignored in the present environment of AIDS and other dreaded diseases.

It is of further note that a major difficulty in performing endoscopic surgery is that the size of the endoscope's insertion member and consequently the number of instrument or operating channels therein is severely limited by the internal anatomy of the patient. The smaller passages in the gastrointestinal tract form blocks which in some cases must be forcibly dilated to enable passage of the endoscope. Such forcible entry causes trauma or pain to patient.

OBJECTS OF THE INVENTION

An object of the present invention is to provide a device and a related method for facilitating sterile endoscopic surgery.

Another object of the present invention is to provide such a device and related method which reduce the time spent on procedures to ensure sterility of endoscopes.

Another, more particular, object of the present invention is to provide such a device and related method which are easy to use.

A further particular object of the present invention is to provide such a device which is simple and relatively inexpensive to manufacture.

Yet a further object of the present invention is to provide an improved endoscopic operating procedure which facilitates the introduction of surgical instruments into a patient.

SUMMARY OF THE INVENTION

A device utilizable with an endoscope to promote sterility comprises, in accordance with the present invention, a substantially thin-walled elongate tubular sheath made of a flexible material such as rubber, the sheath having a use configuration with an inner diameter larger than an outer diameter of an insertion member of the endoscope, whereby the sheath may be removably disposed about such insertion member to substantially surround same prior to insertion of the insertion member into a patient. The device further comprises a transparent cap member and an element or elements for attaching the cap member in a fluid tight seal to a distal end of the sheath so that the cap member covers a distal end of the insertion member of the endoscope.

According to another feature of the present invention, the endoscopic device also comprises a securing component on the sheath for facilitating attachment thereof in a fluid tight seal to the insertion member of the endoscope and for concomitantly facilitating subsequent removal of the sheath from the insertion member of the endoscope.

The securing component may specifically comprise at least one pair of cooperating zip-lock elements extending longitudinally along the sheath. More specifically, the sheath may have a longitudinally extending slit, the cooperating zip-lock elements being disposed on opposite sides of the slit to close the slit and thereby form the use configuration of the endoscopic sterility enhancement device. In addition, the sheath may be provided with an elongate membrane attached to an inner surface of the sheath along opposite sides of the slit to define a substantially closed elongate cylindrical chamber for receiving the insertion member of the endoscope.

Alternatively, the securing component includes a cylindrical air-tight chamber incorporated into the sheath and means attached to the sheath for alternately inflating and deflating the air-tight chamber.

Pursuant to an alternative feature of the present invention, the sheath is initially rolled back upon itself from a proximal end to the cap member at the distal end. To install the sheath on the insertion member of the endoscope, the sheath is unrolleld from its initial configuration to the use configuration.

According to another feature of the present invention, the endoscopic sterility enhancement device includes structure for defining a biopsy channel in or on the sheath. The term "biopsy channel" is used herein to mean any channel through which endoscopic instruments may be inserted. Such instruments include, without limitation, biopsy forceps, graspers, scissors, coagulators, laser fibers, staplers, injectors, clamping forceps, irrigation and suction tubes, cauterization devices, etc.

The structure defining a biopsy channel may include an ancillary tube attached to the sheath and extending longitudinally therealong for receiving an endoscopic operating instrument. The ancillary tube is preferably made of a flexible substantially elastic material.

Pursuant to a particular feature of the present invention, the ancillary tube is initially in a collapsed state and is expandable upon insertion of the operating instrument into the tube. Alternatively, or additionally, in the event that the sheath is provided with a plurality of ancillary tubes defining respective biopsy channels, the ancillary tube has a bendable but form-maintaining substantially cylindrical wall. This structure is especially useful in the event that suction is to be applied via the ancillary tube.

Pursuant to another particular feature of the present invention, the ancillary tube is disposed inside a wall of the sheath.

In accordance with yet another feature of the present invention, a fastener is provided for attaching the sheath to the insertion member at the distal end thereof. Specifically, the fastener includes the cap member.

A method for performing an endoscopic surgical operation comprises, in accordance with the present invention, the steps of (a) providing an endoscope having an insertion member with means for transmitting visual information from a distal end of the insertion member to a proximal end thereof, (b) providing a tubular sheath defining a main chamber, (c) disposing the sheath about the insertion member to enclose at least a distal end portion of the sheath in a fluid tight seal inside the chamber, (d) providing a transparent cap member at a distal end of the sheath to close the distal end of the chamber in a fluid tight seal, and (e) inserting the insertion member with the sheath into a patient. The visual information from the insertion member is then used in a susbequent step (f) to locate a surgical site within the patient. Upon the locating of the surgical site, a surgeon withdraws the insertion member from the patient in a later step (g). The sheath is then removed from the insertion member (step (h)).

Pursuant to another feature of the present invention, the sheath has an ancillary tube which defines an elongate channel extending longitudinally alongside the chamber. In that event, the method further comprises the step of (i) upon the locating of the surgical site and prior to the withdrawal of the insertion member from the patient, inserting a surgical instrument having an elongate shaft into the channel and sliding the shaft along the channel so that an operating tip of the surgical instrument protrudes from the channel at the distal end of the insertion member. In a subsequent step (j), a surgeon performs a surgical operation at the surgical site with the surgical instrument. Upon the performance of the surgical operation, the surgical instrument is preferably, but not necessarily, withdrawn from the biopsy channel prior to withdrawal of the insertion member from the patient.

As discussed hereinabove, the sheath may be disposed about the insertion member of the endoscope by unfurling the sheath from an initial rolled-up configuration. Preferably, the cap member is already attached to the sheath in this particular method of applying the sheath to the endoscope's insertion member.

Alternatively, the sheath may include a zip-lock type seal and the step of disposing the sheath about the insertion member of the endoscope includes the step of closing the zip-lock seal.

As yet another alternative, the sheath includes a cylindrical balloon component about a main chamber of the sheath. Upon a sliding of the endoscope's insertion member into the sheath, the sheath is tightened about the insertion member by inflating the balloon component.

Preferably, the transparent cap member is attached to the sheath and preferably also to the distal end of the endoscope's insertion member.

An endoscope sheath in accordance with the present invention and the related method facilitates sterile endoscopic surgery. The sheath is disposable and designed so that the outer surfaces of the sheath never come into contact with the endoscope. Accordingly, it is no longer necessary to subject the endoscope to sterilizing soaking procedures. The time of hospital personnel is saved, endoscopes have reduced down times, and costs are lowered.

An endoscope sheath in accordance with the present invention is easy to use. Particularly, the sheath is easy to apply to an insertion member of an endoscope.

Moreover, an endoscope sheath in accordance with the present invention is simple and relatively inexpensive to manufacture.

It is to be further noted that the present invention will most likely increase the useful lives of endoscopes, that is, will increase the number of operations in which the endoscopes are used. The wear and tear on the endoscopes arising from non-operation handling is reduced because the endoscopes need not be handled so much outside of the operating.

Yet another advantage of the present invention is to provide an improved endoscopic operating procedure which facilitates the introduction of surgical instruments into a patient. Insofar as an endoscope need not have biopsy channels and requires only the optical fibers and/or electrical leads for the transmission of light and visual information, the diameter of the insertion portion of the endoscope is reduced. Inasmuch as the biopsy channels are collapsed during insertion of the endoscope and expand only upon insertion of the endoscopic operating instruments, the width or thickness during an initial insertion operation is reduced. Moreover, the subsequent insertion of the operating instrument(s) involves only an incremental widening of the internal passageways of the patient through which the endoscope winds. This incremental insertion technique increases the number of instruments which may be inserted simultaneously into a patient along the endoscope path.

An endoscope sheath in accordance with the present invention thus not only facilitates the maintenance of sterile conditions but also enhances the reach of endoscopic surgery.

BRIEF DESCRIPTION OF THE DRAWING

FIG. 1 is a perspective view, on a fore-shortened scale, of an endoscope sheath assembly in accordance with the present invention.

FIG. 2 is an end view of a sheath member of the endoscope sheath assembly of FIG. 1, showing the sheath member in an opened configuration.

FIG. 3 is an end view of the sheath member of FIG. 2, showing the sheath member in a closed, use, configuration.

FIG. 4 is a partial cross-sectional view taken transversely to a longitudinal axis of the sheath of FIG. 1.

FIG. 5 is a perspective view of another endoscope sheath assembly in accordance with the present invention.

FIG. 6 is a partial longitudinal cross-sectional view taken at the distal end of an endoscope sheath assembly in accordance with the present invention.

FIG. 7 is a perspective view, on a fore-shortened scale, of a further endoscope sheath assembly in accordance with the present invention.

FIG. 8 is a side perspective view of the endoscope sheath assembly of FIG. 7, attached to an endoscope pursuant to the present invention.

FIG. 9 is an end elevational view of the endoscope sheath assembly of FIG. 7, showing a sheath member with collapsed biopsy channels and a deflated cylindrical balloon-like element for attaching the sheath assembly to an endoscope.

FIG. 10 is a view similar to FIG. 9, showing the biopsy channels expanded and the balloon attachment element inflated.

FIG. 11 is an end elevational view of a modified endoscope sheath assembly in accordance with the present invention.

FIGS. 12A–12C show successive stages in the securing to an endoscope of another sheath assembly in accordance with the present invention.

FIGS. 13A and 13B show successive steps in the removal of an intestinal polyp via an endoscopic procedure in accordance with the present invention.

DETAILED DESCRIPTION

As illustrated in FIGS. 1-4, a disposable sheath assembly 20 for an insertion member of an endoscope comprises a substantially thin-walled elongate tubular sheath 22 made of a strong flexible material such as rubber. Sheath 22 has a use configuration, shown particularly in FIG. 3, with an inner diameter d1 larger than an outer diameter of the endoscope insertion member, whereby the sheath may be removably disposed about the insertion member to substantially surround the insertion member prior to insertion thereof into a patient.

As shown in FIG. 1, sheath assembly 20 further comprises a transparent end cap 24 provided with an annular mounting ring 26 for attaching the end cap to the distal end of sheath 22 and the distal end of the insertion member of an endoscope. Ring 26 serves to fasten transparent cap 24 in a fluid tight seal to sheath 22 so that the cap covers a distal end of the endoscope insertion member.

End cap 24 is preferably attached to a distal end of sheath 22 during manufacture (see FIG. 5), so that an elongate cylindrical chamber defined by sheath 22 and cap 24 for receiving the insertion member or shaft of an endoscope is open only at a proximal end (the left hand side in FIG. 1). Fastening ring 26 is provided on an internal surface with at least one formation for enabling a removable attachment of end cap 24 and the distal end of sheath 22 to the distal end of the insertion member of an endoscope. Such a releaseable connector may take the form of a rib or groove (see FIG. 6), a screw thread or other known structure. Alternatively, ring 26 may be dimensioned to facilitate attachment thereof and of cap 24 to the distal end of an endoscope insertion member via a force-lock fit.

As shown in FIGS. 2 and 3, sheath 22 is formed with a longitudinally extending slit 28 and is provided with an internal membrane 30 extending longitudinally the length of the sheath. Membrane 30 is secured along its longitudinal edges 32 and 34 to an inner surface 36 of sheath 22. Membrane 30 serves as a protective barrier to prevent bacteria and virus particles on an outer surface of sheath 22 from coming into contact with an endoscope during a removal of the endoscope from sheath assembly 20 upon the completion of an endoscopic procedure.

In an alternative conceptualization of sheath assembly 20, membrane 30 and a portion of sheath 22 extending from the joint at longitudinal edge 32 to the joint at longitudinal edge 34 constitutes a tubular sheath member, whereas a remaining portion of sheath 22 extending from longitudinal edge 34 constitutes a locking or closure flap 38.

Sheath 22 is provided on an inner surface of flap 38 with a pair of longitudinally extending ribs or beads 40 and 42 which cooperate with respective longitudinally extending grooves 44 and 46 on an outer surface of sheath 22 opposite slit 28 to close sheath 22 in a fluid tight seal. Ribs 40 and 42 are pressed into grooves 44 and 46 by a pressure applied longitudinally from a distal end of sheath 22 to a proximal end thereof. This pressure may be applied manually with a simple hand contact or may be facilitated by the provision of a zipper mechanism (not illustrated). As illustrated in FIG. 3, sheath 22 has a substantially smooth external surface upon a closure stroke which presses ribs 40 and 42 into grooves 44 and 46.

Zip-lock ribs 40 and 42 and grooves 44 and 46 serve to facilitate attachment or securement of sheath 22 to an endoscope insertion member in a fluid tight seal prior to an endoscopic surgical operation and to concomitantly facilitate subsequent removal of the sheath from the insertion member of the endoscope after the termination of the operation.

Sheath 22 is provided internally with at least one longitudinally extending channel 48 which serves as a biopsy channel, namely, as a channel through which endoscopic instruments may be inserted during endoscopic surgery. Such instruments include, without limitation, biopsy forceps, graspers, scissors, coagulators, laser fibers, staplers, injectors, clamping forceps, irrigation and suction tubes, cauterization devices, etc.

Sheath 22 is made of a strong, flexible and substantially elastic material such as rubber. In the event that channel 48 is to be used for suction, sheath 22 is constructed so that channel 48 maintains its tubular form. Maintaining the form of channel 48 may be ensured, for example, by the embedding of a reinforcing tube (not illustrated) in the material of sheath 22. However, such a tube is not deemed to be necessary in the event that the material of sheath 22 is sufficiently strong.

As illustrated in FIG. 5, another disposable sheath assembly 50 for providing sanitary protection for the insertion member of an endoscope comprises a substantially thin-walled elongate tubular sheath 52 made of a strong flexible material such as rubber. Sheath 52 has a use configuration with an inner diameter d2 larger than an outer diameter of the endoscope insertion member, whereby the sheath may be removably disposed about the insertion member to substantially surround the insertion member prior to insertion thereof into a patient.

Sheath assembly 50 additionally comprises a transparent end cap 54 provided with an annular mounting ring 56 which serves in part to attach the end cap in a fluid tight seal to the distal end of sheath 52. Ring 56 also serves to fasten the distal end of sheath 52 to the distal end of the insertion member of an endoscope. To perform that function, ring 56 is provided on an internal surface with at least one formation (not illustrated) for enabling a removable attachment of end cap 54 and the distal end of sheath 52 to the distal end of the insertion member of an endoscope. Such a releaseable connector may take the form of a rib or groove (see FIG. 6), a screw thread or other known structure. Alternatively, ring 56 may be dimensioned to facilitate attachment thereof and of cap 54 to the distal end of an endoscope insertion member via a force-lock fit.

As further illustrated in FIG. 5, sheath 52 is formed with a longitudinally extending slit 58 and is provided with an internal membrane 60 extending longitudinally the length of the sheath. As described hereinabove with reference to membrane 30 in FIGS. 1-4, membrane 60 is secured along its longitudinal edges to an inner surface 66 of sheath 52. Membrane 60 serves as a protective barrier to prevent bacteria and virus particles on an outer surface of sheath 52 from coming into contact with an endoscope during a removal of the endoscope from sheath assembly 50 upon the completion of an endoscopic procedure.

Like sheath 22, sheath 52 is provided with one or more longitudinally extending ribs 70 which cooperate with respective longitudinally extending grooves 72 to close sheath 52 in a fluid tight seal. Ribs 70 are pressed into grooves 72 by a pressure applied longitudinally from a distal end of sheath 52 to a proximal end thereof. This pressure may be applied manually with a simple hand contact or may be facilitated by the provision of a zipper mechanism (not illustrated).

As depicted in FIG. 5, sheath assembly 50 incorporates a plurality of flexible webs 74 which are attached to an outer surface of sheath 52 to define respective, substantially tubular, biopsy channels 76 for the deployment of endoscopic surgical instruments during an endoscopic surgical operation. Initially, webs 74 are collapsed upon the outer surface of sheath 52, thereby minimizing at the outset of an endoscopic operation the effective outer diameter of an endoscopic insertion member. This diameter minimalization facilitates deployment of the endoscope by easing the passage of the endoscope's insertion member through smaller internal orifices of a patient.

Upon deployment of an endoscope with an insertion member enveloped or encased in protective sheath assembly 50, endoscopic surgical instruments (not shown) may be forcibly inserted one at a time through respective biopsy channels 76, the channels being expanded from their initial collapsed or closed configuration to an opened or expanded use configuration during the instrument insertion process. In addition, a flexible but non-collapsible tubular member (not shown) may be inserted through a selected channel 76 from the proximal end of sheath assembly 50 to the distal end thereof to serve as a suction channel. Alternatively, sheath 52 is provided with an attached flexible but non-collapsible tubular member 78 for enabling the application of suction to the space immediately distal of end cap 54.

As illustrated in FIG. 6, sheath 52 may be attached to transparent end cap 54 via a ring or annular connector 71 provided along an inner surface 73 with an annular groove 75. During an attachment of sheath assembly 50 to an insertion member of an endoscope, groove 75 receives an annular rib or bead (not shown) provided on the distal end of the insertion member. A distal end of sheath 52 is inserted and held in an annular slot 77 in connector 71.

Other methods of attaching the distal end of sheath 52 to ring 56 (FIG. 5) or of sheath 22 to ring 26 (FIG. 1) are possible. For example, the distal end of sheaths 22 and 52 may be connected via an adhesive layer or an ultrasonic bond to rings 26 and 56, respectively. In addition, rings 26, 56 and 71 may be provided with other formations for releasably connecting the rings and their sheaths 22, 52 to insertion members of endoscopes. Such alternative formations include various snap-lock and screw type elements.

As depicted in FIGS. 7-10, another disposable sheath assembly 80 for an insertion member 81 of an endoscope 83 comprises a substantially thin-walled elongate tubular sheath 82 made of a strong flexible material such as rubber. Sheath assembly 80 further comprises a transparent end cap 84 provided with an annular mounting ring 86 for attaching the end cap to the distal end of sheath 82 and the distal end of insertion member 81 of endoscope 83. Ring 86 serves to fasten transparent cap 84 in a fluid tight seal to sheath 82 so that the cap covers a distal end of insertion member 81.

End cap 84 is preferably attached to a distal end of sheath 82 during manufacture, so that an elongate cylindrical chamber defined by sheath 82 and cap 84 for receiving endoscope insertion member 81 is open only at a proximal end (the left hand side in FIG. 7).

Sheath 82 is provided on an inner side with a balloon member 88 which is inflatable by a pressure source 90 via a tube 92. Balloon 88 is initially in a deflated or collapsed condition. Prior to an endoscopic surgical procedure, endoscope insertion member 81 is inserted into sheath 82, inside balloon 88. Pressure source 90 is connected to balloon 88 via tube 92 and is activated to pressurize balloon 88, inflating the balloon to form a snug contact with endoscope insertion member 81. Balloon 88 thus serves to temporarily connect sheath 82 to insertion member 81.

Sheath assembly 80 includes a plurality of flexible webs 94 which are attached to an outer surface of sheath 82 to define respective, substantially tubular, biopsy channels 96 for the deployment of endoscopic surgical instruments 97 (FIG. 10) during an endoscopic surgical operation. Initially, as depicted in FIG. 9, webs 94 are collapsed upon the outer surface of sheath 82, thereby minimizing at the outset of an endoscopic operation the effective outer diameter of endoscope insertion member 81.

Upon deployment of endoscope 83 with insertion member 81 enveloped or encased in protective sheath assembly 80, endoscopic surgical instruments 97 may be forcibly inserted one at a time through respective biopsy channels 96, the channels being expanded from their initial collapsed or closed configuration (FIG. 9) to an opened or expanded use configuration (FIG. 10) during the instrument insertion process. In addition, a flexible but non-collapsible tubular member 99 may be inserted through a selected channel 96' from the proximal end of sheath assembly 80 to the distal end thereof to serve as a suction channel. Alternatively, sheath 82 is provided with an attached flexible but non-collapsible tubular member 98 for enabling the application of suction to the space immediately distal of end cap 84.

Upon the withdrawal of insertion member 81 with sheath assembly 80 at the end of an endoscopic surgical operation, balloon 88 is deflated via tube 92. Subsequently, sheath 82 is slid off of insertion member 81. A clamp or other releasable closure (not illustrated) may be provided for closing tube 92 and thereby maintaining balloon 88 in an inflated or pressurized state.

FIG. 11 shows another sheath assembly 100 which is a modification of sheath assembly 80 of FIGS. 7-10. Sheath assembly 100 includes a substantially thin-walled elongate tubular sheath 102 made of a strong flexible material such as rubber. Sheath 102 is provided with a plurality of elongate longitudinally oriented indentations 104 for receiving collapsed webs or tubes 106 in a pre-use configuration of the sheath assembly.

Sheath 102 is provided on an inner side with a balloon member 108 which is inflatable by a pressure source (not illustrated) via a tube 110. Balloon 108 is initially in a deflated or collapsed condition. Prior to an endoscopic surgical procedure, an endoscope insertion member is inserted into sheath 102, inside balloon 108. Balloon 108 is then inflated to form a snug contact with the endoscope insertion member. Balloon 108 thus serves to temporarily connect sheath 102 to the insertion member.

Sheath 102 is provided with an attached, flexible but non-collapsible tubular member 112 for enabling the application of suction to the space immediately distal of the distal end of sheath 102.

As illustrated in FIG. 12A, another endoscopic sheath assembly 120 comprises a tubular member 122 attached in a rolled up configuration to a ring member 124. Prior to an endoscopic surgical operation, ring member 124 is connected via a snap-lock fit, a force-lock fit, etc., to the distal end of an endoscope insertion member 126, as shown in FIG. 12B. Tubular sheath member 122 is then unfurled from the rolled up configuration of FIG. 12A to uncover a transparent end cap 128 on ring 124 and to cover the endoscope insertion member 126 from the distal end towards the proximal end thereof. As discussed hereinabove with respect to other embodiments, sheath member 122 may be provided with a multiplicity of collapsed tubular biopsy channels which are expandable by the insertion of endoscopic surgical instruments during an endoscopic operation.

The sheath assemblies described herein provide the possibility in endoscopic surgery of operating with more than one instrument at a time. FIG. 13A depicts a polyp PLP in a patient's colon CLN. An endoscope 130 with a light guide 132 and an image guide 134, surrounded by a disposable sheath 136 is inserted into the colon CLN and is used to detect and investigate the polyp PLP. The polyp has a bent stalk SLK, which makes it difficult to sever the polyp and remove it by conventional endoscopic surgical techniques. Sheath 136, however, has multiple expandable biopsy channels which enables the deployment of two grasping forceps 138 and 140, as shown in FIG. 13A, or both grasping forceps 138 and a cauterization snare 142, as shown in FIG. 13B. Forceps 138 and 140 are used to manipulate polyp PLP from its original position (FIG. 13A) to a more accessible position or orientation (FIG. 13B) which facilitates capture of the polyp by cauterization snare 142. Snare 142 is provided with a capture net 144, as described in commonly owned application Ser. No. 788,035 filed Nov. 5, 1991.

Although the invention has been described in terms of particular embodiments and applications, one of ordinary skill in the art, in light of this teaching, can generate additional embodiments and modifications without departing from the spirit of or exceeding the scope of the claimed invention. For example, the transparent end caps described herein need not be rigid members but may instead take the form of transparent films attached to the distal ends of the sheaths. In addition, the expandable tubular biopsy channels may be provided on the inner surface of a tubular endoscopic sheath member rather than along the other surface thereof. Accordingly, it is to be understood that the drawings and descriptions herein are proferred by way of example to facilitate comprehension of the invention and should not be construed to limit the scope thereof.

What is claimed is:

1. A device utilizable with an endoscope to promote sterility, comprising:
   a substantially thin-walled elongate tubular sheath made of a flexible material, said sheath having a use configuration with an inner diameter larger than an outer diameter of an insertion member of the endoscope, whereby said sheath may be removably disposed about such insertion member to substantially surround same prior to insertion of the insertion member into a patient;
   a transparent element attached in a fluid tight seal to a distal end of said sheath so that said transparent element covers a distal end of the insertion member of the endoscope; and
   securing means on said sheath for facilitating attachment thereof in a fluid tight seal to the insertion member of the endoscope and for concomitantly facilitating subsequent removal of said sheath from the insertion member of the endoscope, said securing means including at least one pair of cooperating zip-lock elements extending longitudinally along said sheath.

2. The device defined in claim 1 wherein said sheath has a longitudinally extending slit, said cooperating zip-lock elements being disposed on opposite sides of said slit to close said slit and form said use configuration.

3. The device defined in claim 1, further comprising means for defining a biopsy channel in or on said sheath.

4. The device defined in claim 3 wherein said means for defining a biopsy channel includes an ancillary tube attached to said sheath and extending longitudinally therealong for receiving an endoscopic operating instrument.

5. The device defined in claim 4 wherein said ancillary tube is made of a flexible substantially elastic material.

6. The device defined in claim 5 wherein said ancillary tube is initially in a collapsed state and is expandable upon insertion of said operating instrument into said tube.

7. The device defined in claim 4 wherein said ancillary tube has a bendable but form-maintaining substantially cylindrical wall.

8. The device defined in claim 4 wherein said ancillary tube is disposed inside a wall of said sheath.

9. The device defined in claim 3 wherein said means for defining a biopsy channel includes a flexible web attached to said sheath and wherein said flexible web is disposed initially in a collapsed state and is expandable upon insertion of said operating instrument into said biopsy channel.

10. The device defined in claim 1, further comprising fastening means for attaching said sheath to said insertion member at said distal end.

11. A method for performing an endoscopic surgical operation, comprising the steps of:

providing an endoscope having an insertion member with means for transmitting visual information from a distal end of said insertion member to a proximal end thereof;

providing a tubular sheath defining a main chamber, said sheath having a transparent element attached to a distal end of said sheath in a fluid tight seal;

disposing said sheath about said insertion member to enclose at least a distal end portion of said sheath in a fluid tight seal inside said chamber, said step of disposing including the step of closing a zip-lock seal on said sheath;

inserting said insertion member with said sheath into a patient;

using visual information obtained from said insertion member via said transparent element to locate a site within the patient;

upon the locating of said site, withdrawing said insertion member from the patient; and removing said sheath from said insertion member.

12. The method defined in claim 11 wherein said sheath has an ancillary tube which defines an elongate channel extending longitudinally alongside said chamber, further comprising the steps of:

upon the locating of said site and prior to the withdrawal of said insertion member from the patient, inserting a surgical instrument having an elongate shaft into said channel and sliding said shaft along said channel so that an operating tip of said surgical instrument protrudes from said channel at the distal end of said insertion member;

performing a surgical operation at said site with said surgical instrument.

13. The method defined in claim 12, further comprising the step of, upon the performance of said surgical operation, withdrawing said surgical instrument from said channel prior to withdrawal of said insertion member from the patient.

14. The method defined in claim 11 wherein said transparent element takes the form of a cap member, further comprising the step of attaching said cap member to said sheath.

15. The method defined in claim 11 wherein said transparent element takes the form of a cap member, further comprising the step of attaching said cap member to said insertion member.

16. A device utilizable with an endoscope, comprising:

a substantially thin-walled elongate tubular sheath made of a flexible material and defining a main channel;

securing means for attaching said tubular sheath to a distal end of an insertion member of the endoscope, said securing means including at least one pair of cooperating zip-lock elements extending longitudinally along said sheath; and means on said sheath separate from said securing means for defining a biopsy channel in or on said sheath said biopsy channel being different from said main channel.

17. The device defined in claim 16 wherein said sheath has a longitudinally extending slit, said cooperating zip-lock elements being disposed on opposite sides of said slit to close said slit, further comprising barrier means on said sheath for inhibiting contamination of the endoscope insertion member by organic matter falling from an outer surface of said sheath upon a separation of said zip-lock elements and an opening of said sheath at a termination of an endoscopic procedure.

18. The device defined in claim 17 wherein said barrier means includes an elongate membrane attached to said sheath along opposite sides of said slit.

19. The device defined in claim 16 wherein said means for defining a biopsy channel includes an ancillary tube attached to said sheath and extending longitudinally therealong for receiving an endoscopic operating instrument.

20. The device defined in claim 19 wherein said ancillary tube is initially in a collapsed state and is expandable upon insertion of said operating instrument into said tube.

21. The device defined in claim 19 wherein said ancillary tube is disposed inside a wall of said sheath.

22. The device defined in claim 16, further comprising a transparent cap member attached to said sheath at the distal end thereof.

23. The device defined in claim 22 wherein said sheath has a longitudinally extending slit, said cooperating zip-lock elements being disposed on opposite sides of said slit to close said slit, further comprising barrier means on said sheath for inhibiting contamination of the endoscope insertion member by organic matter falling from an outer surface of said sheath upon a separation of said zip-lock elements and an opening of said sheath at a termination of an endoscopic procedure.

24. The device defined in claim 23 wherein said barrier means includes an elongate membrane attached to said sheath along opposite sides of said slit.

* * * * *